Figure 1:
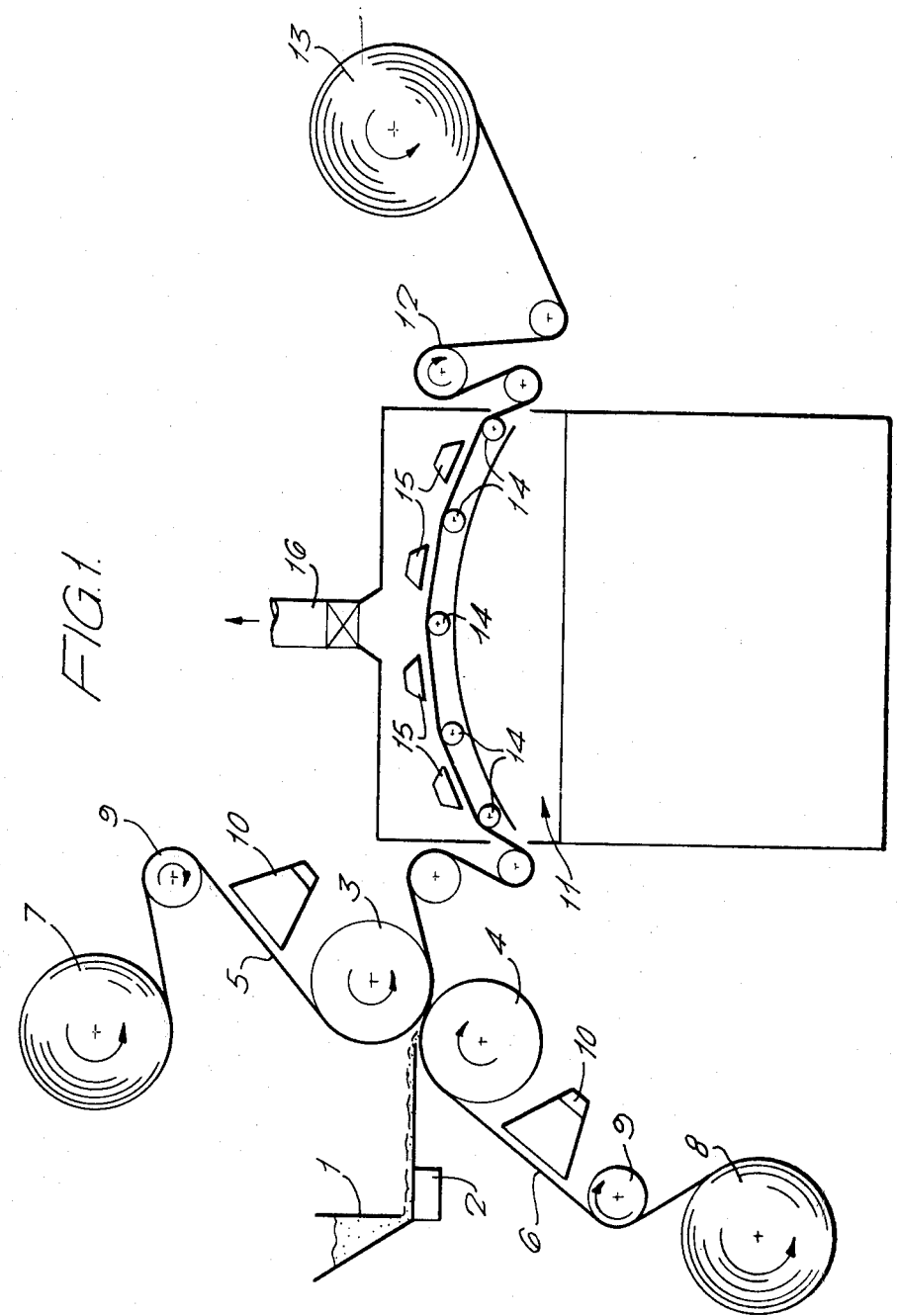

United States Patent [19]  [11]  4,296,234
Mindt, deceased et al.  [45]  Oct. 20, 1981

[54] ABSORBENT MATERIALS

[75] Inventors: Lothar F. O. Mindt, deceased, late of Upper Dean, England; by Peter R. Payne, administrator; George R. Sanderson, both of Bedford, England

[73] Assignee: Lever Brothers Company, New York, N.Y.

[21] Appl. No.: 142,908

[22] Filed: Apr. 23, 1980

Related U.S. Application Data

[63] Continuation of Ser. No. 960,423, Nov. 13, 1978, abandoned, and a continuation of Ser. No. 766,524, Feb. 7, 1977, abandoned.

[30] Foreign Application Priority Data

Dec. 19, 1973 [GB] United Kingdom ............... 58917/73
Dec. 19, 1973 [GB] United Kingdom ............... 58918/73
Jul. 17, 1974 [GB] United Kingdom ............... 31672/74

[51] Int. Cl.$^3$ ....................... A61L 15/00; C08B 31/00
[52] U.S. Cl. ...................................... 536/47; 128/284; 128/285; 128/290 R; 128/296; 536/49; 536/106; 536/108
[58] Field of Search ................... 536/47, 49, 106, 108; 128/284, 285, 290 R, 296

[56] References Cited

U.S. PATENT DOCUMENTS

| | | | |
|---|---|---|---|
| 2,588,463 | 3/1952 | Balassa | 536/50 |
| 2,853,484 | 9/1958 | Lolkema et al. | 536/108 |
| 3,077,468 | 2/1963 | Geurden | 536/87 |
| 3,208,994 | 9/1965 | Fledin | 536/88 |
| 3,467,647 | 9/1969 | Benninga | 536/49 |
| 3,542,759 | 11/1970 | Gelotte et al. | 536/112 |
| 3,622,562 | 11/1971 | Moeigeert | 536/106 |
| 3,670,731 | 6/1972 | Harmon | 525/336 |
| 3,778,431 | 12/1973 | Kightlinger et al. | 536/47 |
| 3,868,955 | 3/1975 | Steiger et al. | 128/296 |
| 3,898,143 | 8/1975 | Assarsson et al. | 128/285 |
| 3,935,099 | 1/1976 | Weaver et al. | 128/290 R |
| 4,117,222 | 9/1978 | Holst et al. | 536/50 |

FOREIGN PATENT DOCUMENTS

| | | | |
|---|---|---|---|
| 859143 | 12/1970 | Canada | 536/106 |
| 949965 | 6/1974 | Canada | 536/106 |
| 960652 | 1/1975 | Canada . | |
| 7701171 | 8/1978 | Netherlands | 538/106 |
| 936039 | 9/1963 | United Kingdom . | |
| 1001481 | 8/1965 | United Kingdom . | |
| 1042864 | 9/1966 | United Kingdom | 536/106 |
| 1183820 | 3/1970 | United Kingdom | 536/108 |
| 1207352 | 9/1970 | United Kingdom . | |
| 1454055 | 10/1976 | United Kingdom . | |

Primary Examiner—Ronald W. Griffin
Attorney, Agent, or Firm—James J. Farrell; Melvin H. Kurtz

[57] ABSTRACT

A highly absorbent material, especially suitable for use in absorbent disposable products such as sanitary towels and tampons, consisting of a substantially water-insoluble cross-linked gelatinized starch, in which the degree of substitution of the cross-linking groups is from 0.001 to 0.04, which is substituted by ionic groups which are associated with mono- or di-valent counterions, and which has a urine retention value of at least 6 g/g.

43 Claims, 4 Drawing Figures

ABSORBENT MATERIALS

This is a continuation application of Ser. No. 960,423, filed Nov. 13, 1978, now abandoned, and a continuation application of Ser. No. 766,524, filed Feb. 7, 1977, now abandoned.

This invention relates to absorbent materials, more especially absorbent materials suitable for use in absorbent disposable products such as, for example, sanitary towels or napkins, tampons and diapers. The invention also relates to processes for producing such materials and to absorbent articles containing such materials.

A number of absorbent materials have been suggested for use in absorbent disposable products, among the first being cellulose in fibre form. Cellulose fibre absorbs by a capillary action and as a result suffers from the serious disadvantage that the absorption is reversible, that is when subjected to pressure the cellulose fibres expel and absorbed liquid.

There has more recently been suggested in U.S. Pat. No. 3,070,095 the use of certain gums in articles to improve their absorbency characteristics. These materials are, however, prone to dissolve in an excess of fluid to give a gummy solution. As a result of this tendency to dissolve, gums have not found extensive use as a primary absorbent in disposable absorbent articles.

To overcome the disadvantage of the absorbent materials described in U.S. Pat. No. 3,070,095, there have been suggested the use of certain absorbent polymers such as the synthetic polymers of U.S. Pat. Nos. 3,669,103 and 3,670,731 and the modified cellulosic fibre described in U.S. Pat. No. 3,589,364. These polymers also have the desirable property of irreversible absorption so that absorbed fluid cannot be squeezed out under the pressures normally associated with the use of absorbent disposables.

We have now discovered that a highly absorbent material, particularly suitable for use in absorbent disposable products such as sanitary towels, tampons and diapers, which is substantially water-insoluble, is capable of absorbing irreversibly and which is substantially dry and non-sticky to the touch in the swollen state, can be obtained from starch.

According to the invention there is provided a highly absorbent material which is substantially dry and non-sticky to the touch in the swollen state being a substantially water-insoluble cross-linked gelatinised starch, in which the degree of substitution of the cross-linking groups is 0.001 to 0.04, which is substituted by ionic groups which are attached to the starch by ether linkages and which groups are associated with mono- or di-valent counterions, and which has a urine retention value of at least 6 g/g.

Gelatinised starch is starch the granules of which have been disrupted. Gelatinised starch which has not been crosslinked is soluble in cold water.

The urine retention value for an absorbent material is determined in the way already well known for water retention values but using a synthetic urine instead of water. Thus in determining the urine retention value the sample to be tested (0.20 g) is weighed out into a pre-weighed sintered glass Gooch crucible. Synthetic urine (5 ml) is added to the sample ensuring that the sample is completely wetted and it is left to soak for 10 minutes before being placed in a centrifuge tube and spun for 10 minutes at 850 rpm in a centrifuge a head radius of 9 cm. The crucible with contents is then reweighed. The urine retention value is expressed as the weight of urine retained per gram of dry absorbent. The formula of synthetic urine, derived from the information given in the Handbook of Clinical Laboratory Data, 2nd Edition, 1968, pages 17–20, is a solution in 5 liters of water of the following:

|  | grams |
| --- | --- |
| $CaCl_2 \cdot 2H_2O$ | 3.680 |
| $K_2SO_4$ | 0.175 |
| KCl | 44.740 |
| KOH | 2.190 |
| $NH_4Cl$ | 6.020 |
| Citric acid | 2.630 |

Water retention values referred to herein were obtained by the same procedure except that distilled water (10 ml) was used instead of the synthetic urine. Experiments have shown that the same urine retention values are obtained using natural urine in place of the synthetic urine. The absorbent materials of this invention have urine retention values of at least 6 g/g and are desirably in the range 8–20 g/g.

The absorbent starch derivatives of this invention are substantially water-insoluble containing at least 90%, preferably at least 95%, of insoluble carbohydrate. The most preferred materials of the invention are those having a water insolubility of 99% or higher.

A feature of the absorbent materials of the present invention is that although the degree of substitution of the cross-linking groups is relatively low (being much smaller, for example, than that of the cross-linked starch products described in Examples 1 to 6 of Canadian Pat. No. 960,652 or the starch product of Example 2 of British Pat. No. 936,039) they are substantially insoluble in water. The more highly cross-linked starch products described in these patents are substantially less absorbent than the materials of the present invention.

The cross-linking of the starch molecules may be effected by ether bridges of the formula —O—R—O— where R is an aliphatic group, which may be substituted by one or more hydroxy groups, containing 1 to 10 carbon atoms. Preferably R is $CH_2CH(OH)CH_2$—, which is the case when the starch is cross-linked using epichlorhydrin as cross-linking agent.

The ionic groups preferably have the formula $Z-R^1-$ where $R^1$ is an alkylene group having 1 to 5 carbon atoms and Z is an anionic group selected from carboxyl, sulphoric or phosphonic groups or a cationic group of the formula

where $R^2$ is hydrogen or lower alkyl, and $R^3$ and $R^4$ are lower alkyl or are alkylene groups linked together to form a five or six-membered heterocyclic ring. Particularly suitable materials are those wherein $R^1$ is an alkylene group containing 1 or 2 carbon atoms and Z is $-COO^-$ and preferred materials are carboxymethylated cross-linked gelatinised starches. The degree of substitution of the ionic groups will generally be at least 0.1 and is desirably at least 0.2 to obtain the preferred higher urine retention values.

When Z is an anionic group the counterion preferably is an alkali metal, alkaline earth metal, ammonium or substituted ammonium ion. The substituted ammonium derivatives may be those in which one or more hydrogen atoms are replaced by $C_{1-4}$ alkyl or $C_{2-4}$ hydroxyalkyl groups or in which the nitrogen atom forms part of a heterocyclic ring. An example of such a substituted ammonium ion is tetramethylammonium. Preferred counterions when Z is an anionic group are the sodium, potassium and ammonium ions. When Z is a cationic group, the counterion may be, for example, chloride, bromide or sulphate.

Particularly preferred absorbent materials of this invention are the sodium and ammonium salts of carboxymethylated epichlorhydrin cross-linked gelatinised starch having a urine retention value of at least 10 g/g and being insoluble in water to the extent of at least 99% by weight.

The invention is also concerned with a process for making the above-described absorbent materials, which process comprises:

1. gelatinising starch;
2. during the gelatinisation or thereafter treating the starch with a cross-linking bifunctional compound to produce a cross-linked gelatinised starch which is substantially insoluble in water and in which the degree of substitution of the cross-linking groups is from 0.001 to 0.04; and
3. During the gelatinisation or thereafter reacting the starch with a monofunctional etherifying agent to substitute the starch by ionic groups which are attached to the starch by ether linkages and which groups are associated with mono- or di-valent counterions, the degree of substitution of the ionic groups being such that the urine retention value of the substituted cross-linked gelatinised starch is at least 6 g/g.

In a preferred way of conducting this process, steps (1) and (2) are carried out by:

(a) forming an aqueous alkaline slurry of starch granules containing the cross-linking bifunctional compound; and
(b) rapidly heating the slurry by applying the slurry to a surface heated to 100°–180° C. to cause gelatinisation of the starch, reaction therewith of the cross-linking bifunctional compound and simultaneous drying, to produce cross-linked gelatinised starch in dry form.

In an alternative process steps (1) and (2) are carried out by:

(c) forming an aqueous slurry of starch granules;
(d) applying the slurry to a surface heated to 100°–180° C. to cause gelatinisation of the starch and simultaneous drying; and
(e) subsequently reacting the gelatinised starch with the cross-linking bifunctional compound in the presence of water and alkali to produce cross-linked gelatinised starch.

In this procedure, the alkali may be included in the slurry. The gelatinisation is very conveniently effected by feeding the aqueous starch slurry onto the surface of a heated drum upon which it can be pressed out into a thin film. The gelatinisation of starch by applying an aqueous slurry thereof to the surface of a heated drum is in itself a very well known process which has been called the cold-swelling starch process (see for example British Pat. No. 787,153).

The reaction of the starch with the monofunctional etherifying agent may be carried out before, during, or after treatment of the starch with the bifunctional cross-linking compound.

To effect the cross-linking of the starch a bifunctional cross-linking agent is used and this may be a compound of the formula $Q-R^5-Y$ where $R^5$ is an alkylene group, which may be substituted by one or more hydroxy groups, containing 1 to 10 carbon atoms, and Q and Y each represent a halogen atom or an epoxy group. Suitable cross-linking agent are epichlorohydrin, dichlorohydrin, dibromohydrin, 1,2-3,4-diepoxybutane, 1,2-7,6-diepoxyoctane, bis-epoxypropylether, 1,4-butane-diol-bis-epoxypropylether. The amount of cross-linking agent employed is that required to give a degree of substitution of the cross-linking groups within the range 0.001 to 0.04, corresponding to one cross-linking group for each 1,000 anhydroglucose units to one cross-linking group for each 25 anhydroglucose units. Preferably an amount of cross-linking agent is employed to give a degree of substitution of the cross-linking groups of from 0.003 to 0.02. The function of the cross-linking agent is to insolubilise the gelatinised starch. Cross-linking significantly beyond that required to insolubilise the gelatinised starch is not employed since increasing amounts of the cross-linking agent gives products having, for a given degree of ionic substitution, lower water and urine retention values.

A preferred method for effecting the cross-linking employs epichlorhydrin and is effected with the gelatinisation of the starch on the surface of a heated drum. In this process the amount of epichlorhydrin (or other volatile cross-linking agent) employed should take account of the loss by vapourisation from the heated surface of part of the cross-linking agent.

For effecting the cross-linking some alkaline substance is required to be present in the reaction mixture, save that when formaldehyde is employed acid conditions are required, as is well known. Sodium hydroxide is quite suitable but other alkalis may of course be used. Since the degree of cross-linking effected is small the amount of alkali required to promote the cross-linking reaction is also small. This has the advantage that in forming the aqueous slurry of starch granules to be applied to the heated surface the concentration of the alkali in the slurry can be insufficient to effect any substantial gelatinisation of the starch before the slurry is heated enabling the slurry to be pumped easily through pipes from a holding vessel to the heated surface where gelatinisation, and, if desired, cross-linking and/or substitution by ionic groups, is effected.

This aqueous slurry desirably contains about 1 to 2 parts by weight of water per part of starch although higher amounts of water could be used.

Where cross-linking is effected after gelatinisation and in the presence of aqueous alkali, the amount of water required to be present can be as low as 0.1 to 0.5 parts per part of starch. A surprising feature of the invention is that although cross-linking of the starch (during or after gelatinisation) can be effected in the presence of the above minor amounts of water, the final cross-linked substantially water-insoluble ionically substituted product nevertheless has high water and urine retention values.

By means of the monofunctional etherifying agent ionic substituent groups are introduced linked to the starch by an ether group. These ionic groups may have the formula $Z-R^1-$ where Z and $R^1$ have the above meanings. The monofunctional etherifying agent may have the formula $Z^1$—$R^1$—X where $R^1$ is an alkylene group of from 1 to 5 carbon atoms, $Z^1$ is an anionic or cationic group Z as defined above, or a group capable of being converted into such an ionic group, and X is a halogen or an epoxy group. However, activated olefinic compounds carrying an ionic group or a group capable of being converted into an ionic group could be used. The group $R^1$ is preferably an alkylene group containing 1 or 2 carbon atoms and $Z^1$ is a carboxylic acid group or a salt thereof. Examples of suitable monofunctional etherifying agents are monochloracetic acid, bromopropionic acid, chloroethylene sulphonic acid, chlorohydroxypropane sulphonic acid, epoxypropane sulphonic acid or 2-chlor-N,N-diethylethylamine hydrochloride. Preferred etherifying agents are monochloracetic acid and the sodium salt thereof. When Z is a basic group, this may be quaternised, if desired, prior to etherification of the starch, for example etherification may be conducted with the quaternary ammonium salt formed between epichlorhydrin and triethylamine. Examples of etherifying agents containing an activated olefinic group and a group capable of being converted into an ionic group, eg with alkali, are acrylamide, acrylonitrile and ethyl acrylate. The etherification is carried out in the presence of alkali. Sodium hydroxide is the preferred alkali. The introduction of the ionic groups increases the urine retention value of the starch derivative. The substitution by ionic groups is effected to such degree as to give a salt having a urine retention value of at least 6 g/g.

It will be appreciated from the above that the actual urine retention value of the product obtained after step (3) is dependent both on the cross-linking and on the ionic-substitution stages. These steps are preferably effected in such manner as to produce an ionically substituted cross-linked gelatinised starch having a urine retention value of at least 8 g/g, more preferably 10-20 g/g. Generally speaking, the substitution by ionic groups should be carried out to result in a degree of substitution of at least 0.1, preferably at least 0.2.

When the substitution stage results in a salt of a carboxylic starch derivative, the process preferably also comprises the additional steps of:

4. treating said starch derivative with an acid to convert the carboxyl groups into their acid form;
5. washing said acid form of the starch derivative with water to remove any soluble salts; and
6. neutralising the acid form of the starch derivative with an alkali to reconvert the starch derivative into an ionic form as an alkali metal, alkaline earth metal, ammonium or substituted ammonium salt.

Conversion of the carboxy group to its acid form and subsequent neutralisation has the advantage that the washing and subsequent drying are facilitated on account of the low water retention of the acid form. Preferably in step (6) the acid form of the starch derivative is neutralised with excess ammonia solution whereafter by heating excess ammonia is removed and the ammonium salt dried.

The starch derivatives of this invention may be obtained from, for example, potato starch, maize starch, wheat starch or tapioca starch.

The invention also relates to liquid absorbent articles containing the absorbent material of the invention, including that prepared by the process of the invention. The liquid absorbent article may comprise a fibrous carrier or support for the absorbent material, such as a woven or unwoven material such as cotton cloth, rayon, wool, surgical gauze or paper as well as cellulosic fluff, on or within which the absorbent material is supported. The absorbent material may be spread on the carrier or it may be mixed with loose fibres to make a composite fluff or wadding which can be enclosed between cover sheets of paper or cloth. The article may also be in the form of a laminate. In a particular form, the carrier comprises two sheets between which the absorbent material is sandwiched.

The absorbent materials of this invention are also useful in other fields, for example as a drying agent; for absorbing perspiration; as a litter material for pets; as a water reservoir agent, eg in horticultural use; and as a carrier for various materials, eg perfumes.

The preparation of absorbent materials in accordance with the invention will now be described with reference to the following Examples 1 to 19 given by way of illustration only.

In these examples the bed volumes of the products obtained at various stages of the processes described are referred to. The bed volume of an absorbent material is determined by allowing 1 gram of the material to stand in excess water in a graduated vessel and reading off the swollen volume.

Urine and water retention values were obtained as described above and are expressed to the nearest quarter of a unit.

The solubility data for the starch derivatives given in the examples were obtained as follows. The absorbent (1 g) was slurried in distilled water (100 ml) at room temperature with stirring for 15 minutes. The slurry was allowed to stand overnight before filtering. The dissolved carbohydrate in the filtrate was measured by the known colorimetric method employing the use of the phenol/sulphuric acid test for soluble carbohydrate. In these determinations to 1 ml of the sample of the test solution were added 1 ml of phenol solution (5% w/v) followed by 5 ml of concentrated sulphuric acid and the liquids mixed by shaking. After leaving to cool for about an hour the concentration of the soluble carbohydrate was determined using a Unicam SP 800 ultra-violet spectrophotometer from the absorbence at the peak at 483 nm by reference to a glucose standard.

EXAMPLE 1

Potato starch (1,000 g) was slurried in water (950 ml) containing epichlorhydrin (8.4 ml; 1.0% epichlorhydrin by weight of starch). Sodium hydroxide (5 g) in water (50 ml) was added with stirring and the mixture was applied to a heated roller via a feeder roller to form a layer on the surface of the roller of about 0.5 mm thickness. The roller itself was heated using steams at 3.77 bars (140° C.). The cross-linked starch derivative was removed from the roller as a flake material to yield 914 g of product. The soluble content of the product was found to be 25.0 mg/g and the product was found to have a bed volume of 13.5 ml/g. Since about half of the epichlorhydrin was lost by evaporation from the heated roller the degree of substitution of the cross-linking groups was about 0.01.

Sodium hydroxide (34 g) in water (66 ml) followed by monochloracetic acid (39 g) in water (11 ml) was slowly added with stirring to the cross-linked potato starch (100 g) as prepared above. The mixture was aged overnight in a polythene bag. The theoretical degree of substitition was 0.67.

The moist carboxymethyl derivative was repeatedly dispersed in water and filtered until the filtrate was neutral. The highly water swollen washed cake was dried in a forced air oven (70° C.) and milled through a 2 mm screen. The milled product (102.7 g) had a water retention value of 24.75 g/g, a urine retention value of 13.00 g/g, a solubility of 0.6% and a bed volume of 50 ml/g.

EXAMPLE 2

Example 1 was repeated exactly as far as ageing the carboxymethylated mixture in a polythene bag. The theoretical degree of substitution was again 0.67.

The moist carboxymethyl derivative was dispersed in 10 times its weight of 1 N hydrochloric acid and soaked for 15 minutes and then filtered. The gel cake was repeatedly dispersed in water and filtered until the filtrate was substantially free of chloride ions. Ammonium hydroxide, specific gravity 0.910, (70 ml) was mixed with the water swollen washed cake before drying in a forced air oven (70° C.) and milling (2 mm screen). The milled product had a water retention value of 20.00 g/g, a urine retention value of 10.25 g/g, a solubility of 0.3% and a bed volume of 51 ml/g.

EXAMPLE 3

Maize starch (500 g) was slurried in water (475 ml) containing epichlorhydrin (4.2 ml; 1% epichlorhydrin by weight of starch). Sodium hydroxide (2.5 g) in water (25 ml) was added with stirring and the mixture was applied to a heated roller as in Example 1. The cross-linked starch derivative was found to have a bed volume of 8.5 ml/g.

The cross-linked maize starch was carboxymethylated as in Example 1 and the product washed and isolated as the ammonium salt as in Example 2 by treatment first with hydrochloric acid and then ammonium hydroxide. The milled product had a water retention value of 16.25 g/g, a urine retention value of 8.75 g/g, a solubility of 1.5% and a bed volume of 44 ml/g.

EXAMPLE 4

Potato starch (100 g) was slurried in water (80 ml) containing 1,2-7,8-diepoxyoctane (0.8 ml). Sodium hydroxide (0.5 g) in water (20 ml) was added with stirring and the slurry applied to a heated roller as in Example 1. The soluble content of the product was 11.6 mg/g and the bed volume of 15.5 ml/g.

The cross-linked potato starch derivative (60 g) milled through a 2 mm screen was carboxymethylated as in Example 1 and the product, after ageing, was washed and isolated as the ammonium salt as in Example 2. The milled product had a water retention value of 17.25 g/g, a urine retention value of 10.00 g/g, a solubility of 0.5% and a bed volume of 33 ml/g.

EXAMPLE 5

1% Cross-linked potato starch (100 g) as prepared in Example 1 was carboxymethylated as in that example, aged overnight in a polythene bag and treated with 1 N HCl and washed by being repeatedly dispersed in water as in Example 2. To the water swollen washed cake (964 g) was added with stirring a solution of sodium carbonate (16.2 g) in water (100 ml) before drying in a forced air oven (70° C.). The milled product (102.1 g) had a water retention value of 19.25 g/g, a urine retention value of 11.50 g/g, a solubility of 0.8% and a bed volume of 42 ml/g.

EXAMPLE 6

To a cake (878.5 g) of acid washed carboxymethylated cross-linked starch, obtained as in the preceding Example, was added with stirring a solution of magnesium carbonate (16.8 g) in water (100 ml) before drying in a forced air oven (70° C.). The milled product (113.5 g) had a water retention value of 9.25 g/g, a urine retention value of 8.75 g/g, a solubility of 0.6% and a bed volume of 23 ml/g.

EXAMPLE 7

The sodium salt of carboxymethylated cross-linked starch prepared as in Example 1 (20 g) was soaked in 1 M magnesium chloride solution (1,000 ml) with occasional stirring for 24 hours then repeatedly washed and filtered until the filtrate was substantially free of chloride ions and dried in a forced air oven (70° C.). The milled product (16.8 g) had a water retention value of 12.50 g/g, a urine retention value of 10.50 g/g and a bed volume of 29 ml/g.

EXAMPLE 8

Alkali potato starch was prepared exactly as the cross-linked starch in Example 1 except that no epichlorhydrin was added to the slurry before roller drying. Water (20 ml) was sprayed onto the alkali starch (100 g) which was then transferred to a sealable jar where epichlorhydrin (0.17 ml; 0.20% by weight of starch) was added and the jar tightly sealed and placed in an oven at 50° C. for 1 hour. The cross-linked starch product (bed volume 13 ml/g, soluble carbohydrate content 7.0 mg/g; degree of substitution of cross-linking groups of about 0.004) was immediately carboxymethylated as in Example 1, aged overnight, treated with acid and washed as in Example 2 until the filtrate was substantially free of chloride ions and the water swollen cake (1,339 g) ammoniated (70 ml of ammonium hydroxide solution sg 0.910) and dried in a forced air oven (70° C.).

The milled product (108.6 g) had a water retention value of 12.25 g/g, a urine retention value of 9.00 g/g, a solubility of 0.6%, and a bed volume of 28 ml/g.

EXAMPLES 9 TO 11

Alkali potato starch was prepared exactly as the cross-linked starch in Example 1 except that no epichlorhydrin was added to the slurry before roller drying. Water (20 ml) was sprayed onto alkali starch (100 g) which was then transferred to a jar where epichlorhydrin was added as indicated in Table 1 below and the jar tightly sealed and shaken for 0.5 hour then left at room temperature for 22.5 hours. The cross-linked starch products were then immediately carboxymethylated as in Example 1, aged overnight, treated with hydrochloric acid and washed as in Example 2 until the filtrates were substantially chloride free and the water swollen cakes ammoniated (70 ml of ammonium hydroxide solution sg 0.910) and dried in a forced air oven (70° C.).

The milled products were tested for water retention value, urine retention value, solubility and bed volume. The data are given in Table 1.

TABLE 1

| Example | Epichlorhydrin ml | Degree of Substitution | Water Retention Value | Urine Retention Value | Solubility (%) | Bed Volume (ml/g) |
|---|---|---|---|---|---|---|
| 9 | 0.1275 | 0.003 | 17.75 | 12.00 | 0.6 | 41 |
| 10 | 0.1700 | 0.004 | 15.25 | 10.25 | 0.7 | 32 |
| 11 | 0.2550 | 0.006 | 13.25 | 10.00 | 0.5 | 27 |

EXAMPLES 12 TO 16

1% Cross-linked potato starch (100 g) was carboxymethylated as in Example 1 to a degree of substitution as shown in Table 2. The aged moist carboxymethyl derivative was then repeatedly dispersed in distilled water (8 l) and filtered until the filtrate was neutral. The highly water swollen cakes were dried in a forced air oven (70° C.). Urine retention values are given in Table 2.

TABLE 2

| Example | Sodium Hydroxide (g) | Monochloracetic acid (g) | Degree of Substitution | Urine Retention Value |
|---|---|---|---|---|
| 12 | 19.8 | 23.3 | 0.25 | 10.50 |
| 13 | 29.6 | 35.0 | 0.42 | 12.25 |
| 14 | 39.5 | 46.6 | 0.56 | 13.75 |
| 15 | 49.4 | 58.3 | 0.66 | 13.25 |
| 16 | 74.1 | 87.4 | 0.71 | 14.50 |

EXAMPLE 17

Sodium hydroxide (12.5 g) in water (30 ml) followed by acrylamide (8.8 g) in water (30 ml) was slowly added with stirring to 1% cross-linked potato starch (20 g); the theoretical degree of substitution was 1.0. The mixture was aged overnight in a polythene bag then repeatedly dispersed in water (2 l) and filtered until the filtrate was neutral. The highly water swollen cake (704 g) was dried in a forced air oven (70° C.). The carboxyethylated starch product (23 g) had a water retention value of 21.25 g/g, a urine retention value of 11.75 g/g, a solubility of 1.3% and a bed volume of 46 ml/g.

EXAMPLE 18

Triethylamine (85.5 ml), epichlorhydrin (48.4 ml) and water (200 ml) were stirred together for 16 hours to form the quaternary ammonium salt. Potato starch (25 g), epichlorhydrin (0.25 ml) and the quaternary adduct (35 ml) were mixed together for 1 minute and then the suspension dried to a flake on a roller drum drier (heated to 140° C.) upon which gelatinisation, cross-linking and substitution of the starch all took place. The dried flake was milled through a 1 mm screen. The product had a urine retention value of 11.25 g/g. The starch was substituted by quaternised groups of the formula $-CH_2CH(OH)CH_2N^+(C_2H_5)_3Cl^-$.

EXAMPLE 19

0.5% Cross-linked potato starch was prepared exactly as in Example 1 but using half the stated amount of epichlorhydrin. 6 kg of this product were dispersed in aqueous isopropanol (42 l of 91% isopropanol) and heated to 40°–50° C. in a 100 l jacketed reaction vessel. Sodium hydroxide solution (5 kg of 35%) was added and the mixture stirred for 30 minutes. Monochloracetic acid (3 kg of 75%) was added (corresponding to a theoretical degree of substitution 0.67) and the temperature raised to 83° C. and stirring continued for 4 hours. After settling, the organic solvent was partly decanted and the pH of the mixture adjusted to pH 1 using 2 N hydrochloric acid. Acetone was then added and the mass filtered on a suction filter and repeatedly washed with 65% aqueous acetone until the filtrate was free of chloride ions. The damp cake was stirred with an excess of 25% ammonium hydroxide solution and then dried overnight in a vacuum drier at 55° C. and 30 mm Hg. The milled product had a water retention value of 25.00 g/g, a urine retention value of 12.75 g/g, a solubility of 2.6% and a bed volume of 60–80 ml/g.

All the materials produced in carrying out the above Examples were substantially dry and non-sticky to the touch in the swollen state, they absorbed water and urine irreversibly, and in spite of being substantially insoluble in water had high urine retention values which is a desired characteristic of absorbent materials for use with disposable products such as sanitary towels and tampons.

Figure 2:
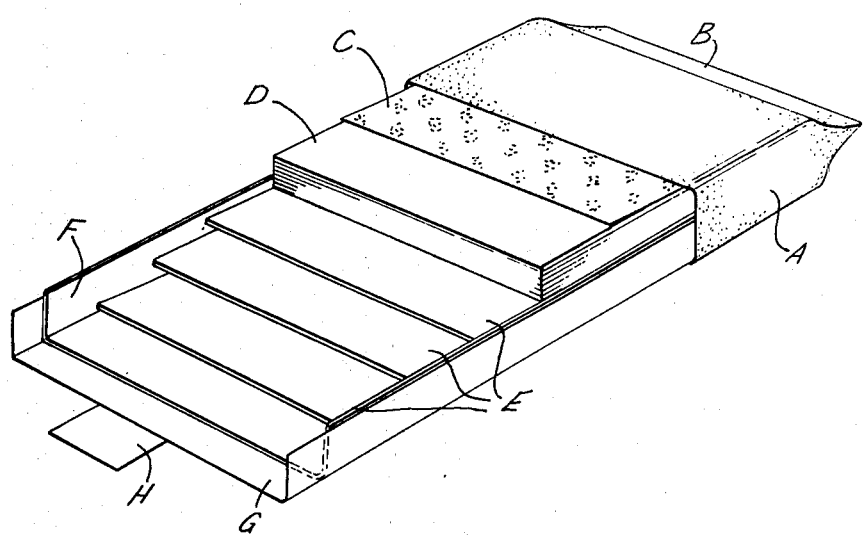
Figure 3:
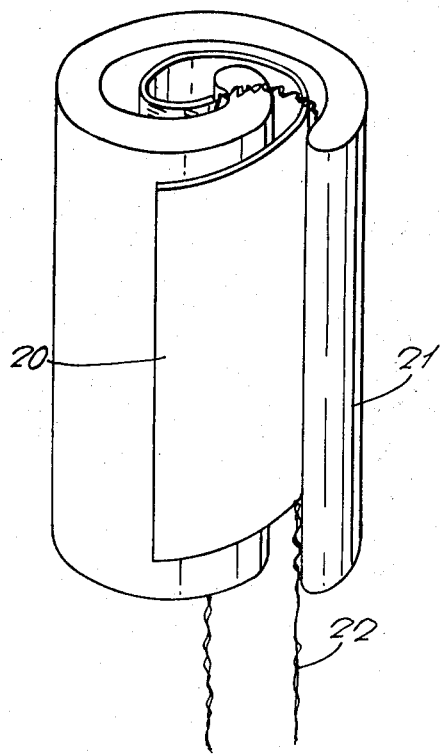
Figure 4:
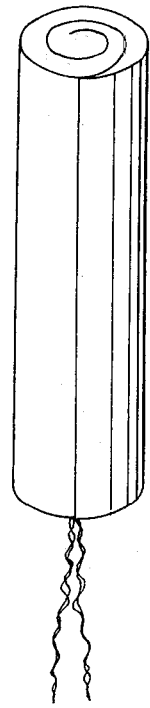

The production of liquid absorbent articles comprising the absorbent material of the invention will now be described with reference to the accompanying diagrammatic drawings in which FIG. 1 shows an apparatus for applying the absorbent material to a carrier layer; FIG. 2 shows a sanitary towel; and FIGS. 3 and 4 show a tampon.

Referring to FIG. 1, a hopper 1 contains particulate absorbent material prepared as described in any of Examples 1 to 19. A vibratory feeder 2 is arranged to feed this material into the nip of a pair of rollers 3, 4 of which the upper roller 3 is of steel and the lower roller 4 of rubber so as to accommodate variations in the size or evenness of the particle layer.

Also feeding into the nip of the rollers 3, 4 are two layers of tissue carrier material 5, 6 supplied from supply rolls 7, 8 via intermediate feed rollers 9. In each case a water spray device 10 is provided which wets the tissue carrier webs 5 and 6 before they reach the nips of rollers 3 and 4.

The wetted carrier layers 5, 6 then receive the particulate absorbent material at the nip of the two rollers 3 and 4 and thereafter feed forward as a composite sandwich ply through a heating chamber 11 which removes moisture from the tissue carriers and absorbent material, round a cooling roller 12 and thence to a storage reel 13.

The heating chamber 11 is an enclosure consisting essentially of an open feedthrough system of rollers 14, radiant heaters 15, and forced extraction exhaust duct 16.

The sanitary towel shown in FIG. 2 consists of a non-woven longitudinal layer rayon fabric outer wrapper A, which may be water soluble. This wrapper is transversely sealed at its ends B.

Immediately below the wrapper is a stain reducing layer C. This is desirably a silicone-treated perforated non-woven layer.

Below the stain-reducing layer is a penetration layer D consisting of 16 layers of multi-ply crepe of 26 grammes per square meter weight. Then below the penetration layer are three layers of absorbent coated sandwich material E made as described above with reference to FIG. 1.

Around the three layers E is a lower absorbent sheet F, which also consists of a tissue carrier layer carrying a continuous deposit of the absorbent material.

Then finally below the absorbent sheet is an impervious polyethylene layer G, and on the outside a gripstrip keeper H which is a conventional silicone-treated adhesive tape for keeping the towel in position in use.

FIGS. 3 and 4 show a tampon formed from a rolled sheet 20 of the absorbent coated sandwich material made as described above with reference to FIG. 1 interspersed with a layer 21 of a long staple fibrous material of cotton, rayon or a cotton/rayon mix. A withdrawal cord 22 is provided.

What is claimed is:

1. A highly absorbent material which is substantially dry and non-sticky to the touch in the swollen state being a substantially water-insoluble cross-linked gelatinised starch, in which the degree of substitution of the cross-linking groups is 0.001 to 0.02, which is substituted by ionic groups which are attached to the starch by ether linkages and which groups are associated with counterions selected from mono- and divalent counterions, and which has a urine retention value of at least 8 g/g.

2. An absorbent material as claimed in claim 1, wherein the degree of substitution of the cross-linking groups is from 0.003 to 0.02.

3. An absorbent material as claimed in claim 1, wherein the cross-linking is effected by ether bridges of the formula —O—R—O— where R is an aliphatic group containing 1 to 10 carbon atoms.

4. An absorbent material as claimed in claim 3, wherein R is —CH$_2$CH(OH)CH$_2$—.

5. An absorbent material as claimed in claim 1, wherein the ionic groups have the formula Z—R$^1$— where R$^1$ is an alkylene group having 1 to 5 carbon atoms and Z is an ionic group selected from anionic groups selected from carboxyl, sulphonic and phosphonic groups and cationic groups of the formula

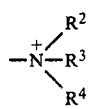

where R$^2$ is selected from hydrogen and lower alkyl, and R$^3$ and R$^4$ are selected from lower alkyl and alkylene groups linked together to form a five or six-membered heterocyclic ring.

6. An absorbent material as claimed in claim 5, wherein R$^1$ is an alkylene group selected from alkylene groups containing 1 and 2 carbon atoms and Z is —COO$^-$.

7. An absorbent material as claimed in claim 6 which is a carboxymethylated cross-linked gelatinised starch.

8. An absorbent material as claimed in claim 1, wherein the degree of substitution of the ionic groups is at least 0.1.

9. An absorbent material as claimed in claim 1, wherein the ionic groups are anionic groups and the counterions are selected from alkali metal, alkaline earth metal, ammonium and substituted ammonium ions.

10. An absorbent material as claimed in claim 9, wherein the counterions are sodium ions.

11. An absorbent material as claimed in claim 9, wherein the counterions are potassium ions.

12. An absorbent material as claimed in claim 9, wherein the counterions are ammonium ions.

13. An absorbent material as claimed in claim 1 which is at least 95% insoluble in water.

14. An absorbent material as claimed in claim 1 which has a urine retention value of from 8 to 20 g/g.

15. An absorbent material as claimed in claim 1 being a sodium or ammonium salt of carboxymethylated epichlorhydrin-cross-linked gelatinised starch having a urine retention value of at least 10 g/g and being insoluble in water to the extent of at least 99% by weight.

16. Process for making an absorbent material as claimed in claim 1 comprising:
   1. gelatinising starch;
   2. during the gelatinisation or thereafter treating the starch with a cross-linking bifunctional compound to produce a cross-linked gelatinised starch which is substantially insoluble in water and in which the degree of substitution of the cross-linking groups is from 0.001 to 0.02; and
   3. during the gelatinisation or thereafter reacting the starch with a monofunctional etherifying agent to substitute the starch by ionic groups which are attached to the starch by ether linkages and which groups are associated with counterions selected from mono- or divalent counterions, the degree of substitution of the ionic groups being such that the urine retention value of the substituted cross-linked gelatinised starch is at least 8 g/g.

17. A process as claimed in claim 16, wherein steps (1) and (2) are carried out by:
   (a) forming an aqueous alkaline slurry of starch granules containing the cross-linking bifunctional compound; and
   (b) rapidly heating the slurry by applying the slurry to a surface heated to 100°–180° C. to cause gelatinisation of the starch, reaction therewith of the cross-linking bifunctional compound and simultaneous drying, to produce cross-linked gelatinised starch in dry form.

18. A process as claimed in claim 16, wherein steps (1) and (2) are carried out by:
   (c) forming an aqueous slurry of starch granules:
   (d) applying the slurry to a surface heated to 100°–180° C. to cause gelatinisation of the starch and simultaneous drying; and
   (e) subsequently reacting the gelatinished starch with the cross-linking bifunctional compound in the presence of water and alkali to produce cross-linked gelatinised starch.

19. A process as claimed in claim 18, wherein the alkali is included in the slurry.

20. A process as claimed in claim 19 in which the concentration of the alkali in the aqueous starch slurry is insufficient to effect any substantial gelatinisation of the starch prior to heating.

21. A process as claimed in claim 16, wherein the gelatinisation and cross-linking of the starch are effected on the surface of a heated drum.

22. A process as claimed in claim 16, wherein the cross-linking bifunctional compound has the formula Q—R$^5$—Y where R$^5$ is an alkylene group containing from 2 to 10 carbon atoms and Q and Y are selected from halogen and epoxy groups.

23. A process as claimed in claim 22, wherein the cross-linking bifunctional compound is epichlorhydrin.

24. A process as claimed in claim 16, wherein the degree of substitution of the cross-linking groups is from 0.003 to 0.02.

25. A process as claimed in claim 16, wherein the ionic groups have the formula Z—R$^1$— where Z and R$^1$ have the meanings defined in claim 5.

26. A process as claimed in claim 25, wherein the monofunctional etherifying agent has the formula $Z^1—R^1—X$ where $R^1$ has the meaning defined in claim 5, $Z^1$ is selected from ionic groups as defined in claim 5 and groups capable of being converted into such ionic groups, and X is selected from halogen and an epoxy group.

27. A process as claimed in claim 26, wherein $R^1$ is an alkylene group selected from alkylene groups containing 1 and 2 carbon atoms and $Z^1$ is selected from carboxylic acid groups and salts thereof.

28. A process as claimed in claim 27, wherein the etherifying agent is selected from monochloracetic acid and the sodium salt thereof.

29. A process as claimed in claim 16, wherein the degree of substitution of the ionic groups is at least 0.1.

30. A process as claimed in claim 16 in which the ionic groups are carboxyl, comprising the additional steps of:
4. treating said starch derivative with an acid to convert the carboxyl groups into their acid form;
5. washing said acid form of the starch derivative with water to remove any soluble salts; and
6. neutralising the acid form of the starch derivative with an alkali to reconvert the starch derivative into an ionic form as a salt selected from alkali metal, alkaline earth metal, ammonium and substituted ammonium salts.

31. A process as claimed in claim 30, wherein in step (6) the acid form of the starch derivative is neutralised with excess ammonia solution whereafter by heating excess ammonia is removed and the ammonium salt dried.

32. A process as claimed in claim 17, wherein the aqueous slurry of starch granules contains about 1 to 2 parts by weight of water per part of starch.

33. A process as claimed in claim 18, wherein in step (c) the amount of water is from 0.1 to 0.5 parts per part of the starch.

34. A process as claimed in claim 16, wherein said counterions in step (3) are sodium ions.

35. A process as claimed in claim 16, wherein the cross-linking and etherification are effected in such manner as to produce an absorbent material having a urine retention value of at least 10 g/g.

36. A process as claimed in claim 16, wherein the cross-linking is effected in such manner as to produce an absorbent material which is at least 95% insoluble in water.

37. A process as claimed in claim 16, wherein the starch derivative produced is selected from the sodium and ammonium salts of carboxymethylated epichlorhydrin-cross-linked gelatinished starch having a urine retention value of at least 10 g/g and being insoluble in water to the extent of at least 99% by weight.

38. A liquid-absorbent article containing an absorbent material as claimed in claim 1.

39. A liquid-absorbent article as claimed in claim 38, wherein the absorbent material is supported on or within a fibrous carrier sheet.

40. A liquid-absorbent article as claimed in claim 38, wherein the absorbent material is sandwiched between two fibrous sheets.

41. A liquid-absorbent article as claimed in claim 39, wherein the carrier is made of paper.

42. A liquid-absorbent article as claimed in claim 38, wherein the article is a sanitary towel.

43. A liquid-absorbent article as claimed in claim 38, wherein the article is a tampon.

* * * * *

UNITED STATES PATENT AND TRADEMARK OFFICE
CERTIFICATE OF CORRECTION

PATENT NO. : 4,296,234
DATED : October 20, 1981
INVENTOR(S) : Mindt et al

It is certified that error appears in the above-identified patent and that said Letters Patent is hereby corrected as shown below:

Column 14, line 5, claim 33, "wherein in step (c)" should read -- wherein in step (e) --.

Signed and Sealed this

Fourth Day of October 1983

[SEAL]

Attest:

GERALD J. MOSSINGHOFF

Attesting Officer    Commissioner of Patents and Trademarks